US010388184B2

(12) United States Patent
Mallisho

(10) Patent No.: US 10,388,184 B2
(45) Date of Patent: Aug. 20, 2019

(54) COMPUTER IMPLEMENTED METHOD AND SYSTEM FOR TRAINING A SUBJECT'S ARTICULATION

(71) Applicant: Amjad Mallisho, Basel (CH)

(72) Inventor: Amjad Mallisho, Basel (CH)

( * ) Notice: Subject to any disclaimer, the term of this patent is extended or adjusted under 35 U.S.C. 154(b) by 169 days.

(21) Appl. No.: 15/588,232

(22) Filed: May 5, 2017

(65) Prior Publication Data

US 2017/0323583 A1 Nov. 9, 2017

(30) Foreign Application Priority Data

May 9, 2016 (CH) .......................................... 604/16
May 9, 2016 (EP) .................................... 16168818

(51) Int. Cl.

*G09B 19/04* (2006.01)
*G10L 25/51* (2013.01)
*G09B 5/06* (2006.01)
*G16H 20/30* (2018.01)

(52) U.S. Cl.

CPC ............... *G09B 19/04* (2013.01); *G09B 5/06* (2013.01); *G10L 25/51* (2013.01); *G16H 20/30* (2018.01)

(58) Field of Classification Search

CPC ...................................................... G09B 19/04
See application file for complete search history.

(56) References Cited

U.S. PATENT DOCUMENTS

2007/0192093 A1* 8/2007 Eskenazi ................ G09B 19/04 704/231
2015/0056580 A1* 2/2015 Kang ...................... G10L 25/51 434/157

FOREIGN PATENT DOCUMENTS

WO 2015/030471 3/2015

* cited by examiner

*Primary Examiner* — Daniel Swerdlow

(57) ABSTRACT

A computer implemented method and system is for training a subject's articulation. The system will receive, access and analyze the speech audio and video data of the subject. The data will be compared to standard speech audio and video data to calculate the deviation of the articulatory parameters between the recorded data of the subject and the standard data. The system will then deconstruct the speech unit and separately play the standard tongue movements, lip movements, jaw movements, and airstream generation. The system will then enable a gradual time converging of the initial separately played standard tongue movements, jaw movements, lip movements and airstream generation in response to a magnitude of the at least articulatory parameter deviation decreasing. Similarly, the system will adapt the display speed and the number of repetitions of these movements to optimize the articulation training.

20 Claims, 1 Drawing Sheet

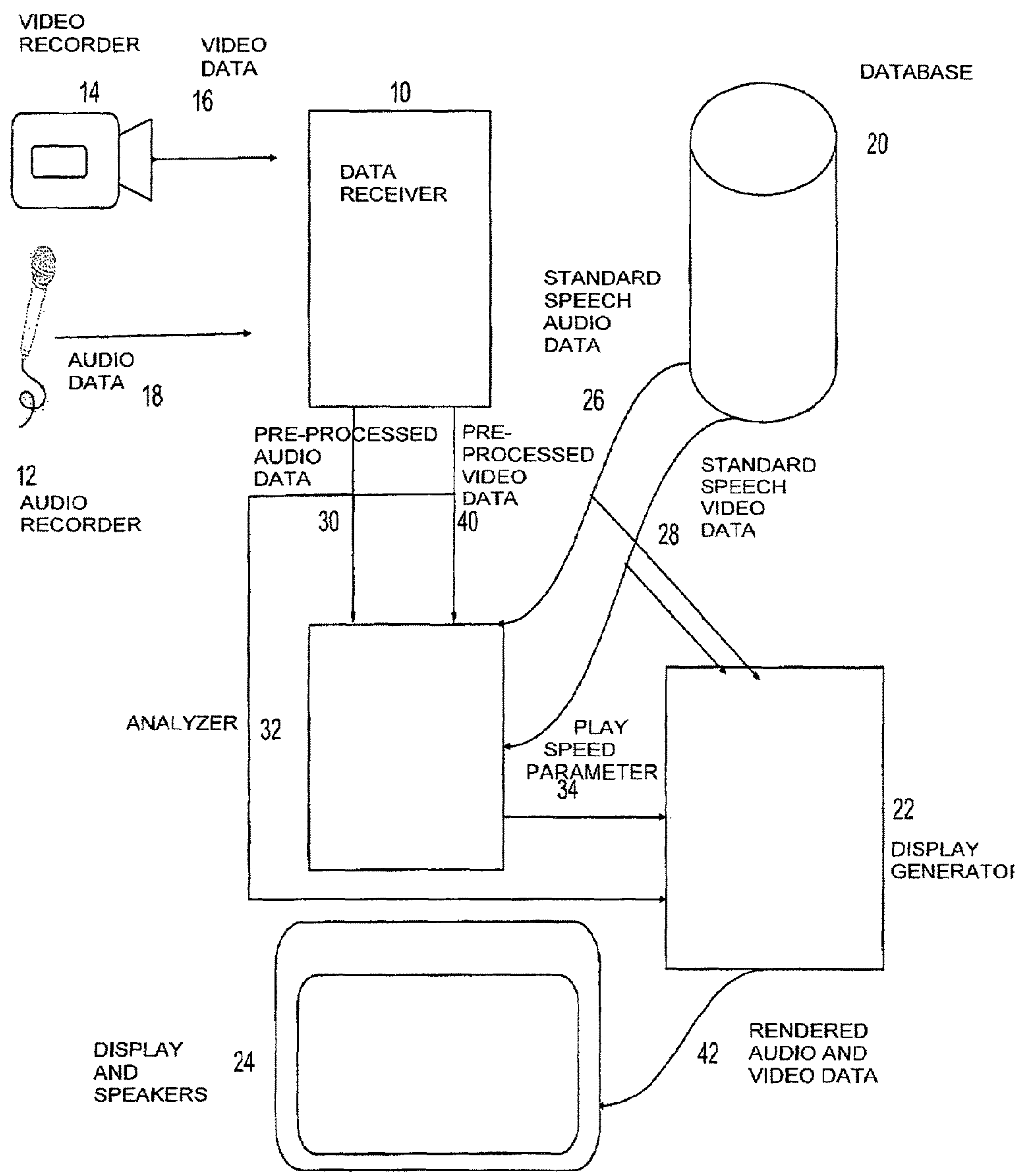
VIDEO
RECORDER
14
VIDEO
DATA
16
10
DATA
RECEIVER
DATABASE
20
AUDIO
DATA
18
12
AUDIO
RECORDER
STANDARD
SPEECH
AUDIO
DATA
26
PRE-PROCESSED
AUDIO
DATA
30
PRE-
PROCESSED
VIDEO
DATA
40
STANDARD
SPEECH
VIDEO
DATA
28
ANALYZER
32
PLAY
SPEED
PARAMETER
34
22
DISPLAY
GENERATOR
DISPLAY
AND
SPEAKERS
24
42
RENDERED
AUDIO AND
VIDEO DATA

COMPUTER IMPLEMENTED METHOD AND SYSTEM FOR TRAINING A SUBJECT'S ARTICULATION

TECHNICAL FIELD

The aspects of the disclosed embodiments generally relate to a computer implemented method and system for training a subject's articulation.

BACKGROUND OF THE INVENTION

Producing speech sounds requires coordination of air flow from the lungs with movements of the tongue, lips and jaw. Expiration passes through the vocal cords towards the oral and/or nasal cavity where it comes into contact with the tongue and lips. Oscillation of the vocal folds converts expiratory air into intermittent airflow pulses that result in voiced sounds. If the vocal folds are open, allowing air to pass unobstructed, they do not vibrate. Sounds produced this way are voiceless.

The pharyngeal, oral, and nasal cavities of the upper respiratory tract act as resonant chambers which transform the airstream into recognizable sounds with special linguistic functions whose main articulators are the tongue, jaw and lips. Together these generate patterned movements to alter the resonance characteristics of the supra-laryngeal airway. Coordination of all these enables us to perfectly pronounce phonemes, morphemes, syllables, words and sentences in any language.

This coordination is regulated by neural networks in the central nervous system that control both articulation (the sounds themselves) and phonological processes (patterns of sound). For example, certain neurons in a particular network control the tongue to move in a certain way into a certain position and likewise send signals to the lips and jaw to take specific forms and positions as needed.

When optimizing pronunciation or perfecting an accent, new neural networks must be established so as to produce new speech sounds properly. It is not enough to rely on previously developed native-language neural networks; an entirely new set of neural networks must, through mimicry and training, be created later in life, when language learning is more labored than in childhood.

Patients suffering from speech disorders or speech impairments also benefit from rebuilding of speech-related neural networks that either never developed sufficient due to congenital deficiencies, or are the result of brain injuries or diseases that impair coordination of the speech organs.

SUMMARY OF THE INVENTION

The present invention provides method and system for establishing new neural networks in human subjects as well as repairing or replacing damaged or inadequate ones. The methods provide an effective tool for improving articulation and pronunciation as well as for treating speech disorders. Thus, the methods provided herein relate to training and/or improving a subjects' articulation, e.g. for learning a foreign language or for training or training down an accent. Moreover, the invention may also relate to medicine, namely to neurology and speech therapy. Methods can be provided for the rehabilitation of patients with speech disorders or speech impediments.

The methods and systems described herein can be implemented using a computer program product having a program code that enables users to work independently and at their own pace.

In this aspect, a computer program product having a program code causing a computer to implement the method described herein is provided.

BRIEF DESCRIPTION OF THE DRAWINGS

FIG. 1 provides a schematic illustration of a system for training a subject's articulation.

DETAILED DESCRIPTION OF THE INVENTION

Unless defined otherwise, all technical and scientific terms used herein have the same meanings as commonly understood by one of ordinary skill in the art to which this invention belongs.

Although similar or equivalent methods and materials to those described herein can be used in the practice or testing of the invention, suitable methods and materials are described below. All publications, patent applications, patents, and other references mentioned herein are incorporated by reference in their entirety. In case of conflict, the present specification, including definitions, will prevail. The materials, methods, and examples are illustrative only and not intended to be limiting.

The term "speech impediments" as used herein comprise, accent, lisping and slurred speech.

The term "speech disorder" as used herein comprises, without being limited to, apraxia of speech and developmental verbal dyspraxia. Apraxia of speech (AOS) is a neurologic speech disorder wherein the subject has an impaired capacity to plan or program sensorimotor commands necessary for directing movements resulting in the correct articulation of speech sounds. Patients suffering from apraxia typically show symptoms of inconsistent articulatory errors and groping oral movements to locate the correct articulatory position. With increasing word and phrase length, errors increase. Adults as well as children may be affected. Adult subjects often acquire a apraxia through lesions of the brain, e.g., due to stroke, tumors, acquired brain injuries, or neurodegenerative diseases, including, without being limited to, Cerebral infarction, Parkinson's disease, Alzheimer's disease, Brain tumors or Huntington's disease.

In some embodiments, apraxia of speech is accompanied by aphasia. In some embodiments, apraxia of speech is accompanied by oral apraxia, i.e., the inability to perform volitional tasks with the oral structures not involving speech, including puckering the lips.

A "speech sound" as used herein comprises, without being limited to, a sound, a phone, a phoneme or a morpheme. A "sound" may be a vowel or a consonant and/or combinations thereof.

The term "speech sound unit" as used herein comprises, without being limited to, a sound, a phone, a phoneme, a morpheme, a syllable, a word and/or a sentence or combinations thereof. It may include several speech sounds as defined above.

Various aspects of the invention are described in further detail below. It is understood that the various embodiments, preferences and ranges may be combined at will. Further, depending of the specific embodiment, selected definitions, embodiments or ranges may not apply.

A computer implemented method and system for training a subject's articulation, comprising the steps of:

receiving subject speech audio data of speech of the subject;

accessing standard speech audio data;

analyzing the subject speech audio data to determine at least one articulatory parameter deviation between the standard speech audio data and the subject speech audio data;

playing a display of standard speech articulatory motion at a display speed for training the subject;

adapting the display speed based on the at least one articulatory parameter deviation, receiving subject speech audio and video data of speech of the subject;

accessing standard speech audio and video data;

analyzing the subject speech audio and video data to determine at least one articulatory parameter deviation between the standard speech audio and video data and the subject speech audio and video data;

playing a display of standard speech articulatory motion at a display speed for training the subject.

In this aspect, a computer program is provided which comprises code means adapted to, when executed on a computer, performing methods as described herein. The methods are useful for improving a human subject's articulation. In some embodiments, the method comprises receiving subject speech audio data of speech of the subject. In embodiments, the speech audio data includes a speech sound unit dataset. In embodiments, the method also includes receiving subject speech video data of speech of the subject. In some embodiments, the video data includes a tongue movement dataset corresponding to a tongue movement deconstructed from the speech sound unit, a lip and/or jaw movement dataset corresponding to a lip and jaw movement deconstructed from the speech sound unit and/or an airstream generation dataset corresponding to an airstream generation deconstructed from the speech sound unit.

In embodiments, the method includes playing a display of standard speech articulatory motion at a display speed for training the subject. In embodiments, the playing step is via a user interaction structure (e.g. display and speakers). The standard speech articulatory motion pre-defines an extended tongue time interval associated to the tongue movement, an extended lip time interval associated to the lip and jaw movement and an extended airstream time interval associated to the airstream generation.

In embodiments, the playing step includes providing a visual representation of the tongue movement dataset over the predefined extended tongue time interval. In embodiments, the method includes capturing a motion of a tongue of the subject during the extended tongue time interval (e.g. using a video camera or other sensor (such as Electromagnetic Articulograph (EMA), motion capture sensors, etc.).

In embodiments, the playing step includes a visual representation of the lip and jaw movement dataset over the predefined extended lip time interval. In some embodiments, motion of a lip of the subject is captured during the extended lip and jaw time interval.

In embodiments, the method includes analyzing the subject speech audio and video data to determine at least one articulatory parameter deviation between the standard speech audio and video data and the subject speech audio and video data. The analyzing step includes comparing the captured motion of the lip and jaw of the subject to the lip and jaw movement dataset to determine at least one articulatory parameter deviation.

In embodiments, the method includes adapting the display speed based on the at least one articulatory parameter deviation if a deviation between the captured motion of the lip of the subject and the lip and jaw movement dataset is identified. In embodiments, the adapting step includes decreasing the predefined tongue time interval, the predefined lip time interval and the predefined airstream time interval.

In embodiments, the playing step includes providing a visual representation of the airstream generation over the predefined extended airstream time interval, decreasing the predefined tongue time interval, the predefined lip time interval and the predefined airstream time interval.

In some embodiments, the method includes repeating the receiving, analyzing, playing and adapting steps.

The visual representations in the playing step can particularly be provided on a screen of the computer running the computer program.

The user interaction structure can be a graphical user interface (GUI) or any other user interface.

For capturing the motion of the subject's lip and optionally the subject's tongue a camera can be used. Alternatively or additionally, the lip and/or tongue can be provided with motion sensors. The computer program then evaluates a signal of the camera and/or of the motion sensors for the comparison.

The method has the effect that the subject is enabled to correctly and efficiently coordinate the movements required for a target articulation of a speech sound unit. After identifying a speech sound unit to exercise, the according unit is deconstructed into a tongue movement, a lip and jaw movement and an airstream generation. An extended time interval is associated to each of the movements and airstream generation. The subject then performs the different movements and airstream generation in any order over the extended time interval, i.e., the subject performs a predefined movement and/or airstream generation in slow motion. The predefined tongue time intervals are decreased as to finally reach a time interval identical to a real time interval of the speech sound unit. The term "real time" as used herein can relate to timing of an average native speaker in everyday speak.

The speech sound unit may be a sound, a phone, a phoneme, a morpheme, a syllable, a word and/or a sentence or a combination thereof.

In one embodiment, a visual representation of the tongue movement is provided to the subject in a visual representation of the lip and jaw movement is provided to the subject and/or a visual representation of the airstream generation is provided to the subject. Such visual representations may e.g. be provided by means of pictures, sketches, video, computer animations or a computer program as disclosed herein.

Preferably, said visual representations in the playing step involve a color coding corresponding to the intensity of the respective movement. The intensity of the movement refers to the extension of the motion of the articulator i.e., the tongue or the lips, in a specific direction.

Thus, in one embodiment, said visual representation of the tongue movement comprises a color coding corresponding to an intensity of the tongue movement.

In one embodiment, said visual representation of the lip and jaw movement comprises a color coding corresponding to an intensity of the lip and jaw movement. In one embodiment, said visual representation of the airstream generation comprises a color coding corresponding to an intensity of the airstream generation.

Preferably, the visual representation of the tongue movement comprises a slowed tongue movement of the speech sound unit and the visual representation of the slowed tongue movement is accelerated, and/or the visual representation of the lip and jaw movement comprises a slowed lip and jaw movement of the speech sound unit and in step (g)

the visual representation of the slowed lip and jaw movement is accelerated. Like this, the visual representation of the tongue movement can comprise a series of slower than normal tongue movements of the speech unit, which with time can then be gradually accelerated back to a standard pace or everyday pace, as the performance of the subject improves. Similarly, the visual representation of the lip and jaw movement can comprise a series of slower than normal the lip and jaw movements of the speech unit, which with time can then be gradually accelerated back to a standard pace or everyday pace, as the performance of the subject improves. Such slowed visual representation(s) allows the deconstructed elements of the speech sound unit to be exercised in detail which makes an accurate improving of the subject's articulation possible.

Furthermore, preferably, the visual representation of the tongue movement comprises a repeated tongue movement of the speech sound unit, the visual representation of the lip and jaw movement comprises a repeated lip and jaw movement of the speech sound unit and/or in step (f) the visual representation of the airstream generation comprises a repeated airstream generation of the speech sound unit. Such repeated visual representation(s) allow the deconstructed elements of the speech sound unit to be isolated and exercised which enable an efficient practice and fast improvement of the subject's articulation possible.

In preferred embodiments, an acoustic representation of the speech sound unit is provided to the subject over the predefined tongue time interval, over the predefined lip time interval and/or over the predefined airstream time interval.

In some embodiments, are repeated until the predefined tongue time interval, the predefined lip time interval and the predefined airstream time interval are identical to a real time interval of the speech sound unit. Thus, the subject may in some embodiments gradually decrease the respective time intervals until the real time interval of the speech sound unit is reached. The number or repetitions may vary. In some embodiments, additional steps of repetition for any of the method alone are included, as the subject may have particular difficulties. The computer implemented system will identify these difficulties and optimize the repetition and the playing speed, depending on the performance of the subject.

In some embodiments, a chronological overlap between the tongue movement, the airstream generation and the lip and jaw movement. Accordingly, the tongue movement is accompanied by the airstream and/or the lip and jaw movement or the lip and jaw movement is accompanied by tongue movement and/or the airstream. In a preferred embodiment, there will be a chronological overlap all these three movements. The computer implemented system will optimize the overlap depending on the performance of the subject.

In one embodiment, the method further comprises the step of identifying a severity of an articulation defect of the subject. For example, a severe articulation defect may require a longer extended time interval, i.e. in a slower pace, and/or an increased number of repetitions. The articulation defect may be a speech disorder, speech impairment or an accent.

This computer implemented system will efficiently support establishing a biological neural network of a human subject. Such slowed visual representation(s) allows the deconstructed elements of the speech sound unit to be exercised in detail which makes an accurate and efficient establishing of the neural network possible.

Such biological neural network may comprise different cell types, such as neurons with a memory function storing the sound of a word or those which control the movement of muscles, in particular of the jaw, the lips, the tongue and/or the breathing muscles. The establishing of said neural network leads to a learning effect such that the human subject may show improved articulation, has learned the pronunciation of a foreign language or accent, or to the treatment of a speech disorder or a speech impairment. Thereby, the subject gets a visual and acoustic input in a pattern which triggers the establishing or reprogramming of the biological neural network and physically changing the connections between the cells.

Preferably, the subject is repeatedly exposed to simultaneous visual, acoustic and kinesthetic stimuli. Kinesthetically means here, the subject is performing the movement according to guidance or instructions as provided by the system to the subject, e.g. through a user interface, as described further below. The guidance or instructions are in the form of audio, visual instructions such as spoken or written instructions. The respective extended time intervals decrease over time, i.e., the subject is exposed to respective visual representations and acoustic reproductions and kinesthetic representations (while performing the movements) as outlined below at increased speed. Said visual representations may e.g. be provided by means of pictures, sketches, video, computer animations or a computer program as disclosed herein. Much preferred are animations, e.g. via video or computer animations. In embodiments, the analyzer is configured to determine the at least one articulatory parameter deviation as described hereinabove and a subject guidance unit is adaptive to the at least one articulatory parameter deviation so as to provide relevant subject feedback in the guidance. Thus, the guidance provided through the subject guidance unit is focused on one or more defects in the patient speech as identified by the analyzer (e.g. one or more areas of deviations between the subject speech and the standard speech that are embodied in exercise specific guidance to the subject for correcting the one or more areas of deviations). If the tongue movement is deviated from the standard one In preferred embodiments, said the computer implemented system will further guide the steps(s) of:

(i) the subject performing the tongue movement for the predefined tongue time interval;

(ii) the subject performing the lip and jaw movement for the predefined lip time interval; and/or (iii) the subject performing the airstream generation for the predefined airstream time interval.

Such performance step(s) increase the speed of the establishing the neural network. Preferably, all three steps (i) to (iii) are performed by the subject simultaneously. The method steps (i) to (iii) may be performed with or without producing a sound with the vocal cords. Thus, in some embodiments, any of the method steps (i) to (iii) are performed without producing a sound with the vocal cords. In some embodiments, any of the method steps (i) to (iii) are performed while producing a sound with the vocal cords. Typically, such performance steps are repeatedly done. The number or repetitions may vary. In some embodiments, additional steps of repetition for any of the method steps (i) to (iii) alone are included, as the subject may have particular difficulties with any of these steps (i) to (iii). The computer implemented system will optimize the number of repetitions and pace depending on the performance of the subject.

In the computer implemented method and system disclosed herein, i.e. the system for improving a human subject's articulation and establishing a biological neural network of a human subject with speech disorder.

In some embodiments, a motion capture device is used to record the subject's movements when performing the method steps, e.g. via video recording. This may be advantageous for destructing the speech sound unit and identifying a severity of an articulation defect or speech disorder.

In this system, a computer program product is provided, having program code causing a computer to implement any one of the methods disclosed herein when being executed.

In one embodiment, a speech sound produced by a human subject is analyzed by a software and deconstructed into the lip and jaw movement, the tongue movement and/or the airstream generation. This typically involves a signal input, e.g. via video recording for the movements and/or a special recorder of the generated vibration for the airstream.

In some embodiments, the software compares the movement of the lips and jaw of the subject to a predefined standard movement. Such predefined standard movement may e.g. be generated by analyzing data from one or more subjects producing correct speech sound units, such as a native speaker of a language. Depending on the subjects shape and size of the lips and jaw, there will be different standard lips and jaw movements. The software will choose one predefined standard lip and jaw movement tailed to the subjects shape and size of the jaw and lips. Subsequently, the software generates a signal and sends visual representations of the predefined lip and jaw movement to subject and/or auditory instructions. The subject may then correct the movement of the lip and jaw to match the predefined standard movement.

In some embodiments, the software compares the airstream generation of the subject to a predefined standard airstream generation. As above, such predefined standard airstream generation may e.g. be generated by analyzing data from one or more subjects producing correct speech sound units, such as a native speaker of a foreign language. Subsequently, the software generates a signal and sends visual representations of the predefined tongue movement to subject and/or auditory instructions. The subject may then correct the airstream generation to match the predefined standard airstream generation.

In some embodiments, the software compares the speech sound unit produced by the subject to the target speech sound unit. Such predefined target speech sound unit may e.g. be generated by analyzing speech sounds from one or more subjects producing correct speech sound units, such as a native speaker of a foreign language. Said comparison gives guidance on the subject's movement of the tongue. Stored on a database are predefined standard tongue movements and the sounds related to them. The software will determine which tongue movement the subject has performed and choose one predefined standard tongue movement for the subject. Subsequently, the software generates a signal and sends visual representations of the predefined tongue movement to subject and/or auditory instructions. The subject may then correct the movement of the tongue to match the predefined standard tongue movement. The described steps of analyzing, comparison and generating a signal can be applied to all different intervals explained of the method steps described herein.

FIG. 1 provides a schematic illustration of a system for training a subject's articulation. The system includes a video recorder 12, an audio recorder 14, a data receiver 10, a database 20, an analyzer 32, a display generator 22 and a display 24. The audio recorder 12 is configured to capture speech of a subject and to generate corresponding audio data 16. The video recorder 14 is configured to capture video of articulatory motions of a subject, including lip, tongue and/or airway motions, and to generate corresponding video data 18. Although a video recorder 14 is described herein, it is possible that other articulatory motion data 18 could be utilized, such as that generated by an articulatory motion sensor of some kind.

The data receiver 10 is configured to receive the audio and video data 16, 18 and to pre-process the audio and video data 16, 18 to produce pre-processed audio data 30 and pre-processed video data 40. Pre-processing may include various filtering and compression operations.

The database 20 of the system stores therein standard speech audio and video data 26, 28 that represent model speech of a subject without speech issues. The standard speech audio and video data 26, 28 serves as a reference for comparison with the audio and video data 36, 40 of the subject.

An analyzer 32 is configured to receive standard audio and video data 26, 28 and the pre-processed audio and video data 30, 40 of the subject. The analyzer 32 generally includes a comparison engine (not shown) for comparing the standard and subject audio and video data 26, 28, 30, 40 to determine at least one articulatory parameter deviation between the standard speech audio data and video data 26, 28 and the subject speech audio and video data 30, 40. The comparison engine, in embodiments, is configured to use image processing techniques to compare video files and audio processing techniques for comparing audio files. In some embodiments, the image processing techniques include image processing, such as segmentation and comparison, to extract relevant articulatory parameters from the video data 28, 40 such as lip movement parameters, tongue movement parameters and airway parameters as described hereinbefore. The comparison engine is configured to use a trained neural network for comparing the standard and subject audio and video data 26, 28, 30, 40, in accordance with various embodiments. The analyzer 32 is configured to output a play speed parameter 34 based on the at least one articulatory parameter deviation as described further below. WO 2015030471 A1 discloses an exemplary analysis technique that could be used by the analyzer 32 of the present application. This document is hereby incorporated by reference.

The display generator 22 of the system is configured to receive at least the standard audio and video data 26, 28 from the database 20 and to adapt a playback speed thereof based on the at least one articulatory parameter deviation. The at least one articulatory parameter deviation is configured so that the greater the deviation between the subject audio and video data 30, 40 and the standard audio and video data 26, 28, the slower the playback of the standard audio and video data 26, 28 according to the adaptations made by the display generator 22. The display generator 22 is, in some embodiments, configured to receive the subject audio and video data 30, 40 and to adapt playback thereof in order to synchronize with playback speed of the standard audio and video data 26, 28. In embodiments, the display generator 22 is configured to generate a play of the standard and subject audio and video data 26, 28, 30, 40 together so that the subject can view the two plays at the same time. For example, a side by side playback is envisaged. The display generator 22 is configured to output rendered audio and video data 42 for output by the display and speakers 42.

Although the system of FIG. 1 has been described in terms of processing both audio and video data, it is envisaging that just one of these data types could be used to provide useful training for the subject.

While there are shown and described presently preferred embodiments of the invention, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

The invention claimed is:

1. A computer implemented method for training a subject's articulation, comprising the steps of:
   receiving subject speech audio data of speech of the subject;
   accessing standard speech audio data;
   analyzing the subject speech audio data to determine at least one articulatory parameter deviation between the standard speech audio data and the subject speech audio data;
   playing a display of standard speech articulatory motion at a display speed for training the subject;
   adapting the display speed based on the at least one articulatory parameter deviation.

2. The computer implemented method of claim 1, comprising:
   receiving video data of speech of the subject, so that subject speech audio and video data of speech of the subject has been received;
   accessing standard speech video data so that standard speech audio and video data has been accessed; and
   analyzing the subject speech audio and video data to determine the at least one articulatory parameter deviation, which represents a deviation between the standard speech audio and video data and the subject speech audio and video data.

3. The computer implemented method of claim 1, wherein the analyzing comprises using pronunciation analysis methods including a formant analysis method, a Fast Fourier Transform (FFT) spectrum analysis method, linear predictive coding (LPC) waveform analysis or a mel-frequency cepstrum (MFC) analysis.

4. The computer implemented method of claim 1, wherein the analyzing step uses a comparison engine to compare the subject speech audio data and the standard speech audio data.

5. The computer implemented method of claim 2, wherein the analyzing step uses a comparison engine to compare the subject speech audio and video data and the standard speech audio and video data.

6. The computer implemented method of claim 2, wherein the analyzing step uses an image processing technique to assess articulatory movements from the subject speech video data including lip and tongue movements.

7. The computer implemented method of claim 1, wherein the adapting step comprises adapting a number of repetitions in at least one of a session plan and a therapy plan.

8. The computer implemented method of claim 1, wherein the display speed is slower for a higher magnitude articulatory deviation parameter.

9. The computer implemented method of claim 1, comprising cyclically repeating the receiving, accessing, analyzing, playing and adapting steps in a speech training session.

10. The computer implemented method of claim 2, wherein:
   the accessing step comprises accessing standard speech audio and/or video data from a database having a plurality of types of standard speech audio and/or video data, wherein each type of standard speech audio and/or video data is associated with standard anatomic dimensional data associated with at least one speech articulator of a subject;
   the method comprising:
   deriving subject anatomic dimensions associated with at least one speech articulator of the subject from the subject speech audio and/or video data;
   selecting a type of standard speech audio and/or video data from the plurality of types based on the subject anatomic dimensions and the standard anatomic dimensions;
   wherein the analyzing step uses the selected type of standard speech audio and/or video data.

11. The computer implemented method of claim 1, comprising the playing step comprises playing the display of standard speech articulatory motion including a color coding that is dependent on tongue position.

12. The computer implemented method of claim 1, wherein playing the display includes displaying a recorded video of standard speech articulatory motion or a derivation therefrom or displaying an animated video of standard speech articulatory motion.

13. The computer implemented method of claim 1, wherein the playing step includes a substantially synchronized display of standard speech articulatory motion and subject speech articulatory motion with respect to display speed.

14. The computer implemented method of claim 1, wherein the playing comprises initially playing separately standard tongue movements, lip movements, jaw movements, and airstream generation and gradually time converging the initial separately played standard tongue movements, jaw movements, lip movements and airstream generation in response to a magnitude of the at least articulatory parameter deviation decreasing.

15. The computer implemented method of claim 14, wherein the gradually converging includes increasing a degree of time overlap.

16. A system for training a subject's articulation, comprising:
   a data receiver configured to receive subject speech audio data of speech of the subject;
   a database having standard speech audio data stored thereon;
   an analyzer configured to analyze the subject speech audio data to determine at least one articulatory parameter deviation between the standard speech audio data and subject speech audio data accessed from the database;
   a display generator configured to play and display standard speech articulatory motion at a display speed for training the subject;
   an adapter configured to adapt the display speed based on the at least one articulatory parameter deviation.

17. The system of claim 16, wherein
   the data receiver is configured to receive video data of speech of the subject, so that subject speech audio and video data of speech of the subject has been received;
   the database further having standard speech video data stored thereon so that standard speech audio and video data is stored thereon; and
   the analyzer is configured to analyze the subject speech audio and video data to determine the at least one articulatory parameter deviation, which represents a deviation between standard speech audio and video data accessed from the database and the subject speech audio and video data.

18. The system of claim 17 comprising a camera and microphone for capturing the subject speech audio and video data and/or a display device for the display.

19. The system of claim 17, wherein the analyzing step uses an image processing technique to assess articulatory movements from the subject speech video data including lip and tongue movements.

20. A non-transitory machine readable medium comprising computer readable instructions, which, when executed by at least one computer processor, is configured to perform the steps of:

receiving subject speech audio and video data of speech of the subject; accessing standard speech audio and video data from a database;

analyzing the subject speech audio and video data to determine at least one articulatory parameter deviation between the standard speech audio and video data and the subject speech audio and video data;

playing a display of standard speech articulatory motion at a display speed for training the subject; and adapting the display speed based on the at least one articulatory parameter deviation.

* * * * *